United States Patent [19]
Golunski et al.

[11] Patent Number: 5,478,528
[45] Date of Patent: Dec. 26, 1995

[54] METAL OXIDE CATALYST

[75] Inventors: Stanislaw E. Golunski, Reading; John M. Gascoyne, High Wycombe; Anthony Fulford, Cambridge; John W. Jenkins, Reading, all of United Kingdom

[73] Assignee: Johnson Matthey Public Limited Company, London, United Kingdom

[21] Appl. No.: 164,413

[22] Filed: Dec. 19, 1993

[30] Foreign Application Priority Data

Dec. 18, 1992 [GB] United Kingdom .................. 9226453

[51] Int. Cl.⁶ ............................................ G01N 30/95
[52] U.S. Cl. ........................... 422/88; 422/83; 422/94; 502/304; 502/338; 502/339; 502/353; 436/134; 73/23.2
[58] Field of Search ............................. 422/83, 86, 177, 422/98, 88, 94; 436/134; 73/23.2, 31.05; 502/304, 338, 339, 353

[56] References Cited

U.S. PATENT DOCUMENTS

| | | |
|---|---|---|
| 3,637,527 | 1/1972 | Jaffe . |
| 3,972,184 | 8/1976 | Warren ................................ 422/177 |
| 4,149,998 | 4/1979 | Tauster et al. . |
| 4,423,407 | 12/1983 | Zuckerman ............................ 422/98 |
| 4,469,816 | 9/1984 | Armor et al. ........................... 502/333 |
| 4,492,769 | 1/1985 | Blanchard et al. ..................... 502/331 |
| 4,617,794 | 10/1986 | Fujitani et al. .......................... 60/285 |
| 4,808,394 | 2/1989 | Kolts et al. ............................. 502/330 |
| 5,217,692 | 6/1993 | Rump et al. ............................. 422/94 |
| 5,234,883 | 8/1993 | Schaefer-Singlinger et al. . |
| 5,302,350 | 4/1994 | Goswami et al. ...................... 436/134 |

FOREIGN PATENT DOCUMENTS

| | | |
|---|---|---|
| 1319928 | 7/1993 | Canada . |
| 0102067 | 3/1984 | European Pat. Off. . |
| 0127942 | 12/1984 | European Pat. Off. . |
| 0266875 | 5/1988 | European Pat. Off. . |
| 0337730 | 10/1989 | European Pat. Off. . |
| 0507590 | 10/1992 | European Pat. Off. . |
| 2058817 | 5/1971 | France . |
| 2011088 | 7/1979 | United Kingdom . |
| 2013901 | 8/1979 | United Kingdom . |
| 1550274 | 8/1979 | United Kingdom . |
| 2019240 | 10/1979 | United Kingdom . |

OTHER PUBLICATIONS

*Successful Design of Catalysts*, 'Fine Structure of NIvel Gold Catalysts Prepared by Coprecipitation', edited by T. Inui, published by Elsevier Science Publishers B.V., Amsterdam (1988) pp. 33–42.

J. Chem. Soc. Faraday Trans., 1992, 88(4), 'Phase Cooperation between the $ZnFe_2O_4$ and $\alpha-Fe_2O_3$ Phases of Ferrite Catalysts in the Oxidative Dehydrogenation of n–Butenes, Zhang et al., pp. 637–644.

*Catalysis*, edited G. C. Bond and G. Webb, The Royal Society of Chemistry, London (1982), pp. 273–307.

*Journal of Catalysts*, 'Bismuth Molybdate Catalysts. Preparation, Characterization and Activity of Different Compounds in the Bi–Mo–O System', Batist et al., 25, (1972), pp. 1–11.

Primary Examiner—Anthony McFarlane
Attorney, Agent, or Firm—Stevens, Davis, Miller & Mosher

[57] ABSTRACT

A catalyst composed of metal oxide particles among which are uniformly incorporated, in order to reduce the operating temperature of the catalyst, palladium particles.

10 Claims, 1 Drawing Sheet

METAL OXIDE CATALYST

BACKGROUND OF THE INVENTION

FIELD OF THE INVENTION

This invention relates to a metal oxide catalyst, its production, a method of conducting a chemical reaction employing it, and a hazardous gas sensor containing a particular example of it.

It has been discovered how a metal oxide catalyst can be operated at a lower temperature.

SUMMARY OF THE INVENTION

The invention provides a catalyst composed of metal oxide particles among which are uniformly incorporated, in order to reduce the operating temperature of the catalyst, palladium particles.

The invention provides also a process for preparing the catalyst, which process comprises co-precipitating the metal oxide particles and the palladium particles.

The invention also provides a method of conducting a chemical reaction employing the catalyst.

The invention provides also a sensor of hazardous gas at ambient temperature, which sensor comprises means to allow gas to contact the present catalyst wherein the metal oxide comprises iron(III) oxide and means to indicate the rise in temperature of the catalyst if hazardous gas is present.

The invention provides, in a catalyst composed of metal oxide particles, the improvement which comprises incorporating palladium particles uniformly among the metal oxide particles to reduce the operating temperature of the catalyst.

The invention similarly provides, in a method of conducting a chemical reaction employing a catalyst composed of metal oxide particles, the improvement comprising incorporating palladium particles uniformly among the metal oxide particles to reduce the temperature of the reaction.

It has been discovered that the operating temperature of a catalyst composed of metal oxide particles can be reduced by incorporating palladium particles uniformly among them. In this structure, there is high and even interaction between the two sets of particles. This contrasts, for instance, with metal oxide particles whose surface has simply been impregnated with the palladium.

As is conventional in this art, references herein to a catalyst component being palladium embrace the possibility of some or all of it being in the form of the oxide.

DETAILED DESCRIPTION OF THE PREFERRED EMBODIMENTS

Figure 1:
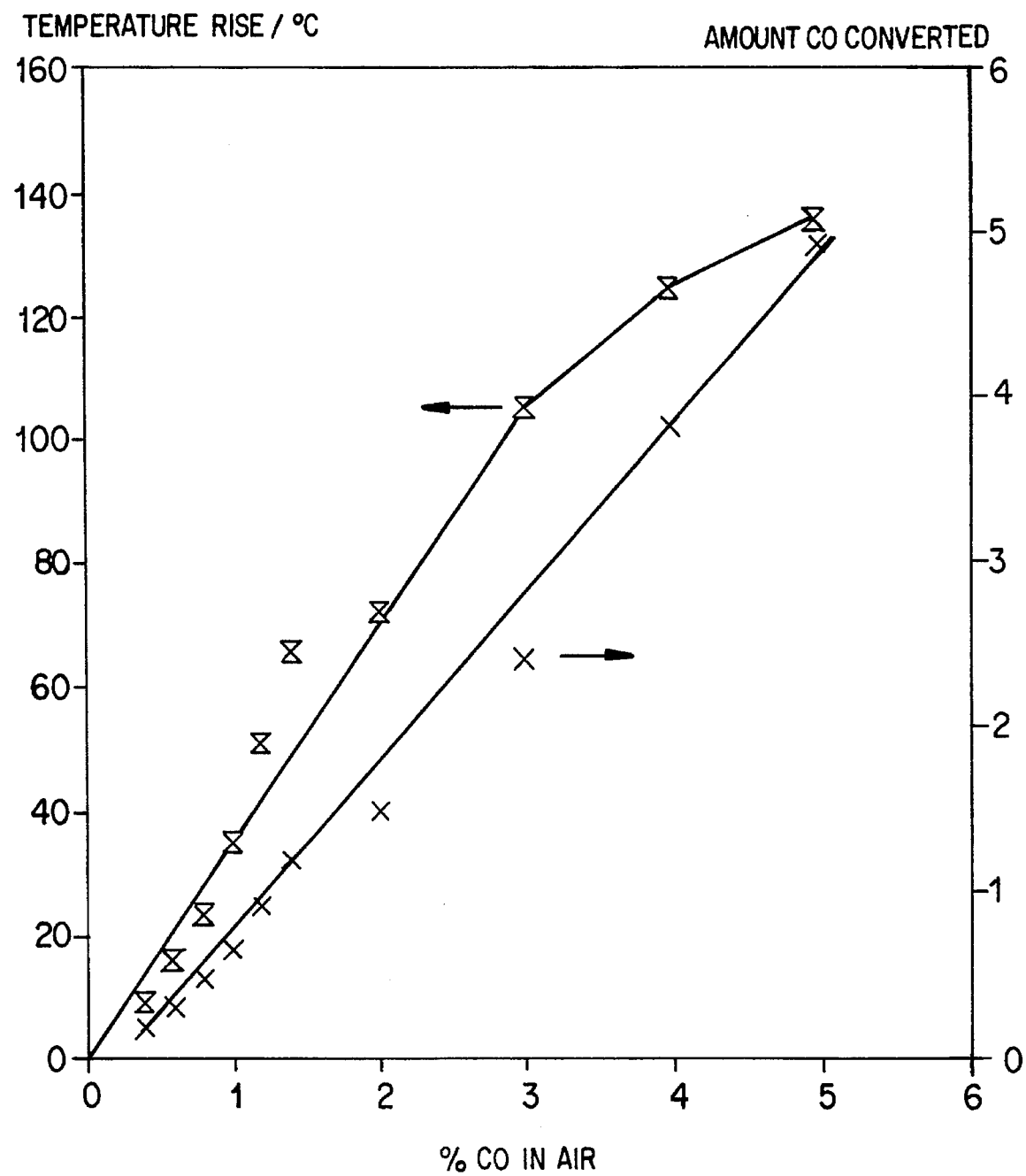
FIG. 1 of the accompanying drawings is a graph showing the effect of varying the CO concentration on CO conversion and the size of the exotherm generated.

The present catalyst usually contains 0.1 to 25%, preferably 1 to 20%, by mass of the palladium particles based on the total mass of the palladium particles and the metal oxide particles.

Additives can be incorporated into the catalyst to convey advantageous properties or avoid disadvantageous properties. The additives can be conventional. The additives can be for instance antimony oxide, or alkali metal ions to improve selectivity in partial oxidation reactions. Additives can be present for instance in amounts of 0.1–50% of the total mass of the catalyst. The lower amounts are appropriate for additives such as alkali metal ions, and the higher for additives such as antimony oxide. The usual antimony oxide can be employed, generally antimony(V) oxide or that known as diantimony tetroxide.

The lowering of the operating temperature of catalysts composed of metal oxide particles is a general phenomenon (providing, of course, thermodynamic considerations do not render this impossible). It is of particular interest where the metal oxide comprises reducible metal oxide, ie the metal oxide is capable of reduction to another oxide of the metal.

The metal oxide may be any which is known to be catalytically active. It can be the oxide of a single metal (for instance iron(III) oxide, cerium(IV) oxide, niobia, magnesium oxide, vanadia or antimony oxide) or a mixture thereof (for instance a mixture of cerium(IV) oxide and antimony oxide or a mixture of vanadia and magnesium oxide), a mixed metal oxide (for instance bismuth molybdate) or a mixture thereof, or a solid solution of one metal oxide in another (which is not necessarily stoichiometric) or a mixture thereof, or a mixture of more than one of these types. The usual antimony oxide can be employed, generally antimony(V) oxide or that known as diantimony tetroxide.

The particle diameter of the catalyst, as measured by sieving, is usually less than 150 microns.

Preferably the catalyst is such that in one or more of the following reactions, it reduces the temperature at which 9% mol conversion occurs by at least 50° C., preferably at least 100° C., compared to that in the case of the catalyst without the palladium:

(A) the conversion of but-1-ene to butadiene using a gas mixture of but-1-ene and air (⅙ by volume) at a flow-rate of 100 $cm^{-3}min^{-1}$ per g of the catalyst;

(B) the conversion of carbon monoxide to carbon dioxide using a gas mixture of carbon monoxide and air (1/99 by volume) at a flow-rate of 2000 $cm^3min^{-1}$ per g of the catalyst;

(C) the conversion of carbon monoxide and steam to carbon dioxide and hydrogen using a gas mixture of by volume 0.1% carbon monoxide, 10% steam and the balance nitrogen, at a flow-rate of 1250 $cm^3min^{-1}$ per g of the catalyst; and (D) the conversion of isobutane to isobutene using a gas mixture of isobutane and air (½ by volume) at a flow-rate of 100 $cm^3min^{-1}$ per g of the catalyst.

The catalyst is preferably that preparable by co-precipitation of the metal oxide particles and the palladium particles. Co-precipitation is a very effective method of incorporating the palladium particles into the metal oxide particles, but an alternative preparation which gives the same result would suffice. The co-precipitation can be carried out in a manner known generally per se, conveniently at ambient temperature. The co-precipitation is preferably carried out so that it occurs in a controlled rather than a sudden manner.

It will be understood that the co-precipitation may produce a precipitate which does not have the metal oxide present as such, but in a form, such as an hydroxide, which is then converted to the metal oxide. The conversion can be accomplished for instance by heating, for example at

50°–500° C.

The chemical reaction in which the present catalyst is employed can be any in which a catalyst without the palladium can be employed. Where the unmodified metal oxide acts as a catalyst in several different reactions, each reaction may be made to occur at a lower operating temperature by means of the present invention. The present reaction is usually conducted at a temperature below 700° C., usually at a temperature within the range of ambient temperature up to 700° C.

By being able to operate a reaction at a lower temperature, a saving of energy can be achieved and the catalyst will tend to last longer. In addition, reactions can now be conducted at ambient temperature which previously required heating the catalyst. In a particular embodiment, the present reaction is conducted at ambient temperature. The low temperature activity of the present catalyst is sustained rather than being transitory. It usually lasts, without regeneration, for at least 5 hours, preferably at least 100 hours, particularly when the catalyst is prepared by co-precipitation.

It is another advantage of the present invention that the catalyst can be employed without prior calcination to activate it. It can simply be washed and dried (at no more than 130° C.) and then used for low temperature catalysis. However, calcination may be deskable to ensure physical stability.

The present chemical reaction is usually oxidation. A preferred reaction is oxidative dehydrogenation, particularly of alkene, especially of but-1-ene to butadiene.

A preferred metal oxide comprises (ie consists of or includes) bismuth molybdate. Another preferred metal oxide comprises iron(III) oxide. A further preferred metal oxide comprises cerium(IV) oxide optionally in admixture with antimony oxide. Catalysts containing these metal oxides can catalyse the reactions normally associated with the unmodified metal oxide from which they are derived.

The catalyst wherein the metal oxide comprises iron(III) oxide is able to oxidise carbon monoxide to carbon dioxide, even at ambient temperature. It is not deactivated by the presence of water vapour. Hence, in an advantageous embodiment it is employed to oxidise carbon monoxide to carbon dioxide in the presence of 0 to 15% water vapour. Gas mixtures referred to in this specification are by volume unless otherwise indicated. This catalyst will also tolerate gas mixtures containing nitrogen oxides and/or sulphur compounds. Hence, in advantageous embodiments it is employed to oxidise carbon monoxide to carbon dioxide in the presence of 0 to 0.2% nitrogen oxides and/or 0 to 0.005% sulphur compounds. It has been found that the rate of CO conversion by this catalyst is linearly dependent on CO concentration, over a range of up to 5% or more by volume in gas such as air. The energy released during reaction is, therefore, proportional to the CO concentration in the gas, making this catalyst particularly suitable to be used for CO sensing. It may also be used to sense, in the absence of CO, other hazardous gases, usually a reducing gas, such as hydrogen or alkene, for instance but-1-ene. In a preferred embodiment, the sensing is at ambient temperature, hence without the need for pellister technology.

The sensor can be of type known in itself. Usually the sensor comprises means to allow gas to contact the catalyst wherein the metal oxide comprises iron(III) oxide and means to indicate the rise in temperature of the catalyst if hazardous gas, especially CO, is present. A particular advantage of sensing at ambient temperature is that the catalyst does not have to be kept at a raised temperature, so avoiding the risk of igniting combustible gas. The present catalyst wherein the metal oxide comprises iron(III) oxide is useful for monitoring the performance of catalytic material for oxidising carbon monoxide to carbon dioxide, for instance in an engine exhaust. Accordingly, in a preferred embodiment, this catalyst is downstream of catalytic material in the exhaust system of an engine, the catalytic material being for oxidising carbon monoxide to carbon dioxide and the sensor monitoring the performance of the catalytic material in this oxidation. This catalyst is particularly suited to automobile applications, and can there be used in on-board diagnostics, such as monitoring the performance of catalytic material for treating the automotive exhaust to combat air pollution. Hence, in a preferred embodiment, the engine is an internal combustion engine in a vehicle and the monitoring indicates when the performance of the catalytic material (for instance a three-way catalyst) falls below a set level. Compared to a prior art low temperature CO oxidation catalyst ($Au/Fe_2O_3$, see page 33 of "Successful Design of Catalysts", edited by T. Inui, published by Elsevier, Amsterdam, 1988), the present catalyst wherein the metal oxide compises iron(III) oxide has the advantages of (a) lower material costs, (b) lower light-off temperature at the same loading of precious metals, and (c) greater resistance to deactivation.

In the presence of CO and $H_2O$, the present catalyst wherein the metal oxide comprises iron(III) oxide functions as a water-gas shift catalyst. This activity begins about 100° C. The catalyst activates in situ, so pre-reduction is not necessary. It can be used in the water-gas shift reaction at, for instance, 100°–200° C.

The present catalysts, particularly those wherein the metal oxide comprises iron(III) oxide or bismuth molybdate, are active in the oxidative dehydrogenation of alkene. The alkene is usually acyclic, and can be straight or branched chain. It generally is of 2–6 carbon atoms. The oxidative dehydrogenation of but-1-ene to butadiene is of particular importance, and the present catalyst effects this at much lower temperatures than expected. This reaction with the present catalyst wherein the metal oxide comprises iron(III) oxide will begin even if the initial temperature of the reactor is below 100° C.; once the reaction has started, for instance after several minutes, it can become self-sustaining without the further supply of heat. In a preferred embodiment, the oxidative dehydrogenation of but-1-ene to butadiene is conducted employing as catalyst the present catalyst wherein the metal oxide comprises iron(III) oxide at a temperature below 200° C., for instance at a temperature between 80° and 200° C.

When the present catalyst wherein the metal oxide comprises iron(III) oxide or bismuth molybdate is employed in the oxidative dehydrogenation of but-1-ene to butadiene, the selectivity to butadiene improves with time on line.

The operating temperature of the present catalyst wherein the metal oxide comprises iron(III) oxide for (a) CO oxidation, (b) water-gas shift, and (c) oxidative dehydrogenation is about 250° C. below that for the corresponding catalyst without the palladium. Similarly, other of the present catalysts, for instance that wherein the metal oxide comprises bismuth molybdate, have a substantially lower minimum operating temperature than the corresponding catalyst without the palladium.

When the metal oxide comprises bismuth molybdate, the oxidative dehydrogenation of but-1-ene to butadiene is preferably conducted at a temperature of 200° to 300° C. This is some 100°–150° C. lower than conventional selective oxidation catalysts require.

The present catalysts, particularly those wherein the metal oxide comprises cerium(IV) oxide, optionally with antimony tetroxide incorporated by mixing into the catalyst, are active in the dehydrogenation, oxidative or not, of alkane of at least 2 carbon atoms to alkene. The alkane is usually acyclic, and can be straight or branched chain. It generally is of 2–6 carbon atoms. A preferred such reaction is the dehydrogenation of isobutane to isobutene.

When the metal oxide comprises cerium(IV) oxide, and as additive diantimony tetroxide is incorporated by mixing into the catalyst, a given yield in the dehydrogenation of isobutane to isobutene occurs about 100° C. lower than in the case of the corresponding catalyst without the palladium. Isobutene is useful for instance for manufacturing the petrol additive methyl t-butyl ether.

Analysis indicates that the present catalyst is usually at least partially amorphous, with metal ions and $Pd^{2+}$ ions on the surface. Chemical analysis of the present dry precipitate wherein the metal oxide is iron(III) oxide shows the presence of $Fe^{3+}$ and $Pd^{2+}$ ions on the surface of a predominantly amorphous bulk. A high degree of interaction between the Pd and Fe phases is inferred from temperature-programmed reduction, which shows substantial shifts (to lower temperatures) of the peaks associated with the reduction of $Fe^{3+}$. Chemical analysis of the present dry precipitate wherein the metal oxide is bismuth molybdate shows a mixture of α-bismuth molybdate ($Bi_2Mo_3O_{12}$; monoclinic) and β-bismuth molybdate ($Bi_2Mo_2O_9$; monoclinic), with there being no evidence of a crystalline Pd-phase. A conventional Bi-Mo-O catalyst (used for comparison in Comparative Example 2 hereafter) is also a mixture of two bismuth molybdates, but these are the β and γ ($Bi_2MoO_6$; orthorhombic) allotropes. Surface analysis of the present dry precipitate wherein the metal oxide is cerium(IV) oxide shows that essentially all the palladium is present as $Pd^{2+}$, and all the cerium as $Ce^{4+}$.

The present catalyst can be employed as the sole catalyst or together with another catalyst, usually comprising one or more of Pt, Pd, Rh and base metal oxide. The present catalyst can be formulated in the usual way to catalyse chemical reactions. When it is employed as sole catalyst, it generally does not need to be dispersed on a separate high surface area carrier. When it is employed together with another catalyst, a high surface area carrier is often useful to carry both catalysts. For instance, the present catalyst can be dispersed on the carrier and, either before or usually afterwards, the other catalyst can be dispersed on the carrier, for instance in the usual way by impregnating with a precursor and calcining to convert the precursor to the other catalyst. The present catalyst itself preferably has a Brunauer Emmett Teller surface area of at least 50, especially at least 100, $m^2g^{-1}$. The catalyst can be employed in the form of pellets. It can be employed on a support, preferably a monolith, for instance a honeycomb monolith. The monolith can be metal, in which case it can readily be heated, for instance by passing an electrical current through the metal. Alternatively the monolith can be ceramic. A separate heater of gas can be utilised up-stream of the catalyst to heat gas to facilitate its reaction on the catalyst.

The invention is illustrated by the accompanying drawings, whose sole FIGURE is described in Example 1 hereafter.

The invention is illustrated by the following Examples.

EXAMPLE 1

A Pd—Fe—O catalyst with a nominal Pd loading of 20% (by mass) was prepared using crystalline $Fe(NO_3)_3.9H_2O$ (52.2 g), aqueous $Pd(NO_3)_3$ (28.0 g of solution≡2.30 g Pd) and solid $Na_2CO_3$ (30.1 g). The two nitrates were added to demineralised water (1 $dm^3$) in a large beaker (2 $dm^3$) fitted with a pH probe and a mechanical stirrer. After dissolving the $Na_2CO_3$ (in 250 $cm^3$ demineralised water), the aqueous precipitant was added to the stirred Pd/Fe solution at a rate of 2 $cm^3min^{-1}$ (using a peristaltic pump).

The Pd/Fe solution was initially orange and had a pH of 1.3, but turned darker as the precipitant was added. The precipitate began to form at a pH of 2.5, and was accompanied by the evolution of carbon dioxide. As the end-point was approached, the suspension became very dark and viscous, and the pH changed more rapidly. At this point, the rate of addition of the precipitant was decreased (to 1 $cm^3min^{-1}$), and then stopped when a pH of 8.5 was reached. The brown gelatinous precipitate was isolated (by filtration), washed thoroughly and dried (110° C.; 16 h). The dry material (12 g) was found to contain 19% Pd (and <0.01% Na) by mass.

A sample (0.20 g) of the dry material (sieved to a particle diameter<150 μm) was tested under a gas mixture of CO/air at a flow rate of 400 $cm^3min^{-1}$. Gas mixtures in this specification are by volume unless otherwise indicated. The initial temperature of the catalyst bed was 50° C. FIG. 1 of the accompanying drawings shows the effect of varying the CO concentration on:

(i) CO conversion (the amount of CO converted as % of total gas flow), (ii) the size of the exotherm generated. (i) shows a linear dependence on CO concentration (over the range 0–5%), indicating that Pd—Fe—O could be used for CO-sensing. (ii) shows a particularly convenient way of doing this (over the range 0–4%).

EXAMPLE 2

Several Pd—Fe—O catalysts with different Pd loadings were prepared by the controlled addition of aqueous $Na_2CO_3$ to a mixed solution of iron(III) nitrate and sodium tetrachloropalladite; the addition of the precipitant was stopped when the pH reached 8.5. An analogous series of prior art $Au/Fe_2O_3$ (page 33 of "Successful Design of Catalysts", edited by T. Inui, published by Elsevier, Amsterdam, 1988) catalysts was prepared by substituting tetrachloroauric acid for the Pd-precursor.

The dry materials were tested under a CO/air (1/99) gas mixture at a gas hourly space velocity of 33000 $h^{-1}$. The conversion of CO was measured as a function of gas inlet temperature. Values for $T_{50}$ (temperature at which CO conversion reaches 50%) were recorded and averaged for several temperature programmed tests. For each loading, the $T_{50}$ value for the Pd-containing catalyst was lower than for the Au-containing analogue (Table 1).

TABLE 1

Light-off ($T_{50}$) temperatures for the oxidation of CO over Pd—Fe—O and $AU/Fe_2O_3$.

| Precious Metal | $T_{50}$/°C. | |
|---|---|---|
| loading / mass % | Pd—Fe—O | $Au/Fe_2O_3$ |
| 0 | 275 | 275 |
| 1 | 75 | 230 |
| 2 | 66 | 120 |
| 4 | 23 | 86 |
| 8 | 60 | 81 |

When the best Au-containing catalyst (8% $Au/Fe_2O_3$) was exposed to the gas mixture at 140° C., the initial CO conversion was 100%, but declined to <20% over a period of 140 hours. The Pd—Fe—O catalysts did not show the same deactivation. Their activity remained at 100% during the first 10 hours, and was still >80% after 140 hours.

EXAMPLE 3

The ability of 20% Pd—Fe—O (nominal composition; prepared as in Example 1) to convert the CO in an exhaust gas was tested at low temperature (100° C.). A sample (1 g) of the dry material was exposed to a simulated mixture of automotive exhaust gas, at an equivalence ratio ($\lambda$) of 0.98 (Table 2) and flow rate of 2 dm$^3$min$^{-1}$. The conversion of CO was 95%, and showed no signs of declining with repeated testing (amounting to a total of 20 hours' use).

TABLE 2

Composition of simulated exhaust gas mixture at $\lambda = 0.98$.

| Component | Concentration / mol % |
|---|---|
| $H_2$ | 0.43 |
| $O_2$ | 0.72 |
| CO | 1.30 |
| $CH_4$ | 0.067 |
| $C_3H_8$ | 0.0223 |
| $C_3H_6$ | 0.0223 |
| $CO_2$ | 15.0 |
| $H_2O$ | 9.2 |
| NO | 0.15 |
| $SO_2$ | 0.002 |
| $N_2$ | balance |

EXAMPLE 4

Samples of 20% Pd—Fe—O (prepared as in Example 1) were aged under a variety of conditions before being re-tested under the exhaust gas mixture (at $\lambda$=0.98; Table 2). The ageing conditions and the activity results are summarised in Table 3.

TABLE 3

Effect of catalyst ageing on CO activity under an exhaust gas at 100° C.

| | Ageing conditions | | | | CO conversion % at $\lambda = 0.98$ |
|---|---|---|---|---|---|
| | $SO_2$ | $H_2O$ | Temperature, °C. | Duration, hour | $H_2$ or $O_2$ | |

| | $SO_2$ | $H_2O$ | Temp. °C. | Dura-tion, hour | $H_2$ or $O_2$ | CO conv. % at $\lambda = 0.98$ |
|---|---|---|---|---|---|---|
| (a) | 0.002% | 10% | 400 | 0.5 | 1% $H_2$ | 0 |
| (b) | 0.002% | 10% | 200 | 5.0 | 1% $O_2$ | 82 |
| (c) | 0.002% | absent | 400 | 0.5 | 1% $O_2$ | 55 |
| (d) | absent | 10% | 200 | 0.5 | 1% $H_2$ | 86 |
| (e) | 0.002% | absent | 200 | 5.0 | 1% $H_2$ | 35 |
| (f) | absent | absent | 400 | 5.0 | 1% $H_2$ | 0 |
| (g) | absent | 10% | 400 | 5.0 | 1% $O_2$ | 75 |
| (h) | absent | absent | 200 | 0.5 | 1% $O_2$ | 93 |

Complete loss of low-temperature activity occurred only when the material was aged under a reducing gas at high temperature (ie samples (a) and (f) in Table 3).

EXAMPLE 5

The ability of 20% Pd—Fe—O (prepared as in Example 1) to catalyse the water-gas shift reaction at low CO concentration (in the presence of a large excess of $H_2O$) was measured over the temperature range 100°–200° C. A sample (2 g) was tested in a spinning-basket reactor (2500 rpm), using a gas mixture containing CO/$H_2O$ (1/100) in nitrogen at a flow rate of 2.5 dm$^3$min$^{-1}$. The results are shown in Table 4.

TABLE 4

Steady-state activity data for water-gas shift reaction. (Inlet and outlet concentrations / mol ppm)

| Catalyst | Temperature °C. | Inlet (CO) | Outlet (CO) | Outlet ($H_2$) |
|---|---|---|---|---|
| 20% Pd—Fe—O | 100 | 998 | 830 | 112 |
| | 110 | 1002 | 818 | 154 |
| | 120 | 998 | 787 | 186 |
| | 150 | 998 | 706 | 251 |
| | 200 | 1000 | 650 | 340 |
| $\alpha$-$Fe_2O_3$ | 100 | 1010 | 998 | 0 |
| | 150 | 999 | 995 | 0 |
| | 250 | 998 | 979 | 0 |
| Fe—O* | 250 | 1006 | 978 | 0 |

*mildly reduced $\alpha$-$Fe_2O_3$ (0.5% $H_2$; 360° C.; 20 min)

The difference between the rate of CO conversion and the rate of $H_2$ release, at temperatures between 100° and 150° C., suggests that 20% Pd—Fe—O was being reduced by the hydrogen being generated. At 200° C., this in situ reduction appeared complete, and the two rates became almost identical. The commercial sample of $\alpha$-$Fe_2O_3$ showed negligible $H_2$ formation under identical conditions, even after mild reduction.

EXAMPLE 6

In order to determine the extent to which water-gas shift can contribute when 20% Pd—Fe—O (prepared as in Example 1) is exposed to an exhaust gas, the CO conversion was measured both in the presence and absence of $O_2$ in the simulated exhaust gas (see Table 2 for composition). At 100° C., the CO conversion dropped substantially (Table 5) when $O_2$ was removed from the simulated exhaust gas; the effect was much less at 165° C. The results show that direct oxidation of CO occurs at the lowest temperatures, but the water-gas shift reaction begins to predominate above ca 150° C.

TABLE 5

Effect of $O_2$ removal from exhaust gas on CO-conversion over 20% Pd—Fe—O.

| | CO-conversion / % | |
|---|---|---|
| Temperature °C. | Full exhaust gas | Exhaust gas without $O_2$ |
| 100 | 95 | 32 |
| 140 | 99 | 43 |
| 165 | 99 | 77 |

EXAMPLE 7

4% Pd—Fe—O (nominal composition) was prepared as described in Example 1, except the mass of Pd in the nitrate precursor was 0.46 g. A sample (1 g) of the dry precipitate was tested under a gas mixture of but-1-ene/air (1/6) at a flow-rate of 100 cm$^3$min$^{-1}$. Unlike the performance expected for catalysts derived from iron oxide (eg see Zhang et al, J. Chem. Soc. Faraday Trans., 88 (1992) 637), Pd—Fe—O showed substantial activity (including oxidative dehydrogenation) at temperatures below 200° C. (Table 6).

TABLE 6

| Temperature °C. | Conversion % | $CO_2$ | Selectivity % | | |
|---|---|---|---|---|---|
| | | | Trans but-2-ene | Cis but-2-ene | butadiene |
| 180 | 74 | 30.5 | 30 | 22 | 4.5 |
| 135 | 61 | 43 | 23 | 18 | 15 |
| 80 | 44.5 | 45 | 17.5 | 15 | 22 |

(molar conversions and selectivities)

At a furnace temperature of 80° C., the catalyst bed temperature rose to ca 130° C. during reaction. The heat generated was then sufficient to sustain the reaction without further heat input from the furnace.

The selectivity of Pd—Fe—O to butadiene improved as a function of time on line (Table 7a), and could be further enhanced by adjusting the butene/air ratio in the gas feed (Table 7b).

TABLE 7

Enhancing oxidative dehydrogenation of butene
over 4% Pd—Fe—O at 100° C.

(a) Effect of conditioning
(activity measured for butene/air = 1/6)

| | Conversion % | $CO_2$ | Selectivity | | |
|---|---|---|---|---|---|
| | | | Trans but-1-ene | Cis but-2-ene | butadiene |
| 2 min on line | 65 | 45 | 14 | 12 | 15 |
| 5 h on line | 54 | 36 | 3 | 2 | 59 |
| * 2 min on line | 70 | 42 | 13 | 11 | 21 |

(b) Effect of gas composition
(activity of sample aged on line for 5 h)

| Butene/Air | Conversion % | $CO_2$ | Selectivity % | | |
|---|---|---|---|---|---|
| | | | Trans but-2-ene | Cis but-2-ene | butadiene |
| 1/6 | 54 | 36 | 3 | 2 | 59 |
| 1/4 | 51 | 28 | 2 | 1 | 69 |
| 1/2 | 23 | 31 | 4 | 5 | 60 |

* after "regeneration" of the 5 h used catalyst under air at 500° C.

COMPARATIVE EXAMPLE 1

In order to assess the significance of the results presented in Example 7, a number of related materials were prepared and tested:

(i) Impregnated 4% Pd—Fe—O was prepared by adding aqueous $Pd(NO_3)_3$ (containing 0.153 g Pd) to FeO(OH) (3.73 g) to form a thick paste, which was heated gently on a hot plate. The warm paste was transferred to an oven (110° C.) for drying (16 h), before calcination (500° C.; air; 2 h).

(ii) Precipitated Pd—O was prepared by adding aqueous $Na_2CO_3$ to aqueous $Pal(NO_3)_3$ (containing 2.30 g Pd). The precipitate was isolated, washed and dried (110° C.; 16 h).

(iii) Precipitated Fe—O was prepared by adding aqueous $Na_2CO_3$ to aqueous $Fe(NO_3)_3.9H_2O$ (52.2 g). The precipitate was isolated, washed and dried (110° C.; 16 h).

(iv) Precipitated 4% $Au/Fe_2O_3$ was prepared by the method described in Example 2.

A sample (1 g) of each material was tested under a gas feed of but-1-ene/air (1/6) at a flow rate of 100 $cm^3min^{-1}$ (Table 8). None of these materials was active at temperatures below 150° C. Between 150° and 200° C., precipitated Pd—O showed reasonable activity, but the selectivity to butadiene was very low. Over a similar temperature range, impregnated 4% Pd—Fe—O was more selective, but the activity was poor; 4% $Au/Fe_2O_3$ showed high initial activity, but this was not sustainable. Precipitated Fe—O needed to be used above 300° C. before the yield of butadiene was comparable to that of precipitated Pd—Fe—O at 80°–100° C.

Table 8

Butene oxidation performance at minimum operating temperature (ie, the minimum temperature at which measurable amounts of product are formed) (T); activity measured after 20 min on line.

| Catalyst | T °C. | Conversion, % | $CO_2$ | Selectivity, % | |
|---|---|---|---|---|---|
| | | | | but-2-ene | butadiene |
| Precipitated Pd—O | 150 | 42 | 54 | 43 | 2.5 |
| Precipitated Fe—O | 300 | 41 | 51 | 14 | 35 |
| Impregnated 4% Pd—Fe—O | 150 | 5 | 30 | 38 | 31.5 |
| Precipitated $Au/Fe_2O_3$ | 150* | 70 | 38 | 30 | 20 |

*rapid deactivation occurs at this temperature

EXAMPLE 8

Pd—Bi—Mo—O, with a nominal Pd-loading of 10% (by mass) and Bi/Mo molar ratio of 2/1, was prepared by co-precipitation. Initially, aqueous $Pd(NO_3)_3$ (containing 0.45 g Pd) was added to a solution of $Bi(NO_3)_3.5H_2O$ (6.06 g) dissolved in 30% $HNO_3$ (20 $cm^3$). Ammonium molybdate (7.86 g dissolved in 10% aqueous ammonia) was then added dropwise, with very rapid stirring; some precipitation occurred during addition. The pH of the resultant suspension was adjusted to 7.4 (using concentrated aqueous ammonia), completing the precipitation of a fine yellow powder. The precipitate was isolated, washed, dried (110° C.; 16 h) and calcined (500° C.; air; 4.5 h).

When a sample (1 g) of this material was tested under but-1-ene/air (1/7) at a flow-rate of 100 $cm^3min^{-1}$, the minimum operating temperature was ca 200° C. The yield of butadiene gradually increased over the first few minutes, before stabilising after 20–25 min (Table 9). This activity was at a temperature 150°–200° C. lower than the minimum expected for mixed-metal oxide catalysts (C. F. Cullis et al in "Catalysis", edited by G. C. Bond and G. Webb, Royal Society of Chemistry, London, 1982, page 273).

TABLE 9

Butene oxidation activity of 10% Pd—Bi—Mo—O
at 200° C., as a function of time on line.

| Elapsed time, min | Conversion, % | $CO_2$ | Selectivity, % | |
|---|---|---|---|---|
| | | | but-2-ene | butadiene |
| 2 | 55 | 30.5 | 24.5 | 45 |
| 25 | 65 | 23 | 19.5 | 57.5 |

TABLE 9-continued

Butene oxidation activity of 10% Pd—Bi—Mo—O at 200° C., as a function of time on line.

| Elapsed time, min | Conversion, % | $CO_2$ | Selectivity, % but-2-ene | butadiene |
|---|---|---|---|---|
| 50 | 60 | 20 | 22 | 58 |

COMPARATIVE EXAMPLE 2

For comparison (to Example 8), an unmodified bismuth molybdate catalyst (in which the molar ratio of Bi/Mo=2/1) was prepared by a standard route (Ph Batist et al, J. Catal., 25 (1972), 1). Ground $Bi(NO_3)_3 \cdot 5H_2O$ (6.06 g) was added to concentrated aqueous ammonia (15 cm$^3$), and stirred for 5 min. The resultant suspension was filtered to isolate the white powder, which was then washed free of ammonia. The powder was added to $H_2MoO_4$ (1.03 g) in distilled water (150 cm$^3$), and the mixture was heated under reflux (18 h). The solid product was isolated, dried (110° C.; 2 h) and calcined (500° C.; 2 h).

A sample of the bismuth molybdate (1 g) was tested at 200° C., under but-1-ene/air (1/7) at a flow-rate of 100 cm$^3$min$^{-1}$ (Table 10a). Some initial activity was observed, but only for the first few minutes. Sustainable activity was not achieved until the temperature was raised to 350°–400° C., when the material functioned as a very selective catalyst for butadiene formation (Table 10b). On lowering the temperature back down to 200° C., no activity was observed.

TABLE 10

Butene oxidation activity of unmodified bismuth molybdate, as a function of time on line.

| Elapsed time, min | Conversion, % | $CO_2$ | Selectivity, % but-2-ene | butadiene |
|---|---|---|---|---|
| (a) 200° C. | | | | |
| 2 | 25 | 3 | 61 | 36 |
| 25 | 3 | 1 | 44 | 55 |
| 50 | 0 | — | — | — |
| (b) 350° C. | | | | |
| 2 | 75 | 8 | 13.5 | 70 |
| 25 | 83 | 5.5 | 14 | 62.5 |
| 45 | 83 | 6.5 | 14 | 67.5 |

EXAMPLE 9

Pd/CeO$_2$, with a nominal Pd-loading of 4% (by mass) was prepared by co-precipitation. A mixed solution was prepared by adding at ambient temperature $Ce(NO_3)_3 \cdot 6H_2O$ (126 g of solid) to aqueous $Pd(NO_3)_3$ (26.04 g of solution=2.0 g Pd). This solution was added dropwise to a boiling solution of NaOH (37.08 g) dissolved in the minimum amount of distilled water required to dissolve it. The resultant suspension was maintained at 100° C. for 1.25 hours. The precipitate was then isolated (by filtration), washed, dried (110° C.; 16 h) and calcined (700° C.; air; 2 h). Elemental analysis of the material showed it to contain 3.87% Pd (and <0.01% Na) by mass.

When a sample (1 g) was tested under either isobutane/N$_2$ (1/5) or isobutane/air (1/2) at a flow-rate of 100 cm$^3$min$^{-1}$, optimum activity for the formation of isobutene occurred at 400° C. (Table 11). The Table also shows that the short-term yield of isobutene could be improved by using a physical mixture of the Pd/CeO$_2$ (0.6 g) and Sb$_2$O$_4$ (0.4 g).

TABLE 11

Conversion of isobutane at 400° C., as a function of time on line (a) Direct dehydrogenation (under isobutane/N$_2$)

| Catalyst | Elapsed Time, min | Conversion, % | Isobutene selectivity % |
|---|---|---|---|
| 4% Pd/CeO$_2$ | 2 | 7.5 | >98 |
| | 20 | 7 | >98 |
| | 35 | 5.5 | >98 |
| Pd/CeO$_2$ + Sb$_2$O$_4$ | 2 | 8.5 | >98 |
| | 20 | 5 | >98 |

(b) Oxidative dehydrogenation (under isobutane/air)

| Catalyst | Elapsed Time, min | Conversion, % | Selectivity, % *CO$_x$ | Isobutene |
|---|---|---|---|---|
| 4% Pd/CeO$_2$ | 2 | 10 | 61 | 39 |
| | 20 | 10 | 58 | 42 |
| 4% Pd/CeO$_2$ + Sb$_2$O$_4$ | 2 | 15 | 45 | 55 |
| | 20 | 7 | 80 | 20 |

*CO$_x$ = CO$_2$ + CO?

COMPARATIVE EXAMPLE 3

For comparison (to Example 9), a physical mixture of CeO$_2$ (0.6 g) and Sb$_2$O$_4$ (0.4 g) was tested under isobutane/N$_2$ (1/5) and isobutane/air (1/2), at flow-rates of 100 cm$^3$min$^{-1}$ (Table 12). The yields of isobutene were much lower than for either 4% Pd/CeO$_2$ or 4% Pd/CeO$_2$+Sb$_2$O$_4$, with negligible activity under isobutane/N$_2$ at temperatures below 500° C.

TABLE 12

Isobutane dehydrogenation activity of CeO$_2$ + Sb$_2$O$_4$ (a) Direct dehydrogenation (under isobutane/N$_2$)

| Temperature, °C. | Maximum isobutane conversion, % |
|---|---|
| 400 | 0 |
| 500 | 1 |
| 550 | 1.5 |

(b) Oxidative dehydrogenation (under isobutane/air) at 400° C.

| Elapsed time, min | Conversion % | Selectivity % CO$_x$ | Isobutene |
|---|---|---|---|
| 2 | 7 | 76 | 11 |
| 20 | 6 | 73 | 15 |

We claim:

1. A sensor of hazardous gas at ambient temperature, which sensor contains a catalyst comprising iron(III) oxide particles among which are uniformly incorporated, in order to reduce the operating temperature of the catalyst, palladium particles, and which sensor also comprises means to allow gas to contact the catalyst and means to indicate the rise in temperature of the catalyst caused by reaction of the gas on the catalyst if the gas is hazardous.

2. A sensor according to claim 1 wherein the hazardous gas is carbon monoxide.

3. A sensor according to claim 2 wherein the catalyst, when sensing, is at a temperature below 200° C.

4. A sensor according to claim 2 wherein the catalyst comprising the iron(III) oxide in the sensor is downstream of catalytic material in the exhaust system of an engine, the catalytic material in the exhaust system being for oxidizing carbon monoxide to carbon dioxide and the sensor monitoring performance of said catalytic material in said oxidizing of carbon monoxide to carbon dioxide.

5. A sensor according to claim 4 wherein the engine is an internal combustion engine in a vehicle, and the monitoring indicates when the performance of the catalytic material falls below a set level.

6. The sensor according to claim 1 wherein the palladium particles are present in an amount of 0.1–25% by mass based on the total mass of the palladium particles and the iron(III) oxide particles.

7. The sensor according to claim 1 wherein the catalyst also comprises bismuth molybdate.

8. The sensor according to claim 1 wherein the catalyst further comprises cerium(IV) oxide.

9. The sensor according to claim 1 wherein the catalyst further comprises antimony oxide as an additive.

10. The sensor according to claim 1 in which the catalyst is preparable by co-precipitation of the iron(III) oxide particles and the palladium particles.

* * * * *